(12) United States Patent
Henry, Jr. et al.

(10) Patent No.: US 9,597,466 B2
(45) Date of Patent: Mar. 21, 2017

(54) AEROSOL DELIVERY SYSTEM AND RELATED METHOD, APPARATUS, AND COMPUTER PROGRAM PRODUCT FOR PROVIDING CONTROL INFORMATION TO AN AEROSOL DELIVERY DEVICE VIA A CARTRIDGE

(71) Applicant: R.J. Reynolds Tobacco Company, Winston-Salem, NC (US)

(72) Inventors: Raymond Charles Henry, Jr., Cary, NC (US); Frederic Philippe Ampolini, Winston-Salem, NC (US)

(73) Assignee: R. J. Reynolds Tobacco Company, Winston-Salem, NC (US)

( * ) Notice: Subject to any disclaimer, the term of this patent is extended or adjusted under 35 U.S.C. 154(b) by 322 days.

(21) Appl. No.: 14/207,016

(22) Filed: Mar. 12, 2014

(65) Prior Publication Data
US 2015/0258289 A1    Sep. 17, 2015

(51) Int. Cl.
*A61M 15/06* (2006.01)
*A24F 47/00* (2006.01)
*A61M 11/04* (2006.01)

(52) U.S. Cl.
CPC .......... *A61M 15/06* (2013.01); *A24F 47/008* (2013.01); *A61M 11/042* (2014.02); *A61M 2205/02* (2013.01); *A61M 2205/33* (2013.01); *A61M 2205/35* (2013.01); *A61M 2205/3673* (2013.01); *A61M 2205/50* (2013.01); *A61M 2205/502* (2013.01); *A61M 2205/52* (2013.01); *A61M 2205/582* (2013.01); *A61M 2205/583* (2013.01);
(Continued)

(58) Field of Classification Search
CPC ...... A61M 15/06; A24F 47/002; A24F 47/008
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report and Written Opinion for International Application No. PCT/US2015/019879 dated May 18, 2015.
(Continued)

*Primary Examiner* — Steven Douglas
*Assistant Examiner* — Kathrynn Lyddane
(74) *Attorney, Agent, or Firm* — Womble Carlyle Sandridge & Rice LLP

(57) ABSTRACT

The present disclosure relates to an aerosol delivery system and methods, apparatuses, and computer program products for providing control information to an aerosol delivery device via a cartridge. For example, a method may include a control body for the aerosol delivery device reading control information carried by a cartridge removably engaged with the control body. The method may further include the control body performing an action based on the control information.

28 Claims, 8 Drawing Sheets

(52) U.S. Cl.
CPC .............. *A61M 2205/6018* (2013.01); *A61M 2205/702* (2013.01); *A61M 2205/8206* (2013.01); *A61M 2205/8212* (2013.01)

(56) References Cited

U.S. PATENT DOCUMENTS

| | | | |
|---|---|---|---|
| 2,104,266 A | 1/1938 | McCormick | |
| 2,805,669 A | 9/1957 | Meriro | |
| 3,200,819 A | 4/1963 | Gilbert | |
| 3,398,754 A | 6/1966 | Tughan | |
| 3,316,919 A | 5/1967 | Green et al. | |
| 3,419,015 A | 12/1968 | Wochnowski | |
| 3,424,171 A | 1/1969 | Rooker | |
| 3,476,118 A | 11/1969 | Luttich | |
| 4,054,145 A | 10/1977 | Berndt et al. | |
| 4,131,117 A | 12/1978 | Kite et al. | |
| 4,150,677 A | 4/1979 | Osborne | |
| 4,190,046 A | 2/1980 | Virag | |
| 4,219,032 A | 8/1980 | Tabatznik et al. | |
| 4,259,970 A | 4/1981 | Green, Jr. | |
| 4,284,089 A | 8/1981 | Ray | |
| 4,303,083 A | 12/1981 | Burruss, Jr. | |
| 4,449,541 A | 5/1984 | Mays et al. | |
| 4,506,682 A | 3/1985 | Muller | |
| 4,635,651 A | 1/1987 | Jacobs | |
| 4,674,519 A | 6/1987 | Keritsis et al. | |
| 4,708,151 A | 11/1987 | Shelar | |
| 4,714,082 A | 12/1987 | Banerjee et al. | |
| 4,735,217 A | 4/1988 | Gerth et al. | |
| 4,756,318 A | 7/1988 | Clearman et al. | |
| 4,771,795 A | 9/1988 | White et al. | |
| 4,776,353 A | 10/1988 | Lilja et al. | |
| 4,793,365 A | 12/1988 | Sensabaugh, Jr. et al. | |
| 4,800,903 A | 1/1989 | Ray et al. | |
| 4,819,665 A | 4/1989 | Roberts et al. | |
| 4,821,749 A | 4/1989 | Toft et al. | |
| 4,830,028 A | 5/1989 | Lawson et al. | |
| 4,836,224 A | 6/1989 | Lawson et al. | |
| 4,836,225 A | 6/1989 | Sudoh | |
| 4,848,374 A | 7/1989 | Chard et al. | |
| 4,848,376 A | 7/1989 | Lilja et al. | |
| 4,874,000 A | 10/1989 | Tamol et al. | |
| 4,880,018 A | 11/1989 | Graves, Jr. et al. | |
| 4,887,619 A | 12/1989 | Burcham, Jr. et al. | |
| 4,907,606 A | 3/1990 | Lilja et al. | |
| 4,913,168 A | 4/1990 | Potter et al. | |
| 4,917,119 A | 4/1990 | Potter et al. | |
| 4,917,128 A | 4/1990 | Clearman et al. | |
| 4,922,901 A | 5/1990 | Brooks et al. | |
| 4,924,888 A | 5/1990 | Perfetti et al. | |
| 4,928,714 A | 5/1990 | Shannon | |
| 4,938,236 A | 7/1990 | Banerjee et al. | |
| 4,941,483 A | 7/1990 | Ridings et al. | |
| 4,941,484 A | 7/1990 | Clapp et al. | |
| 4,945,931 A | 8/1990 | Gori | |
| 4,947,874 A | 8/1990 | Brooks et al. | |
| 4,947,875 A | 8/1990 | Brooks et al. | |
| 4,972,854 A | 11/1990 | Kiernan et al. | |
| 4,972,855 A | 11/1990 | Kuriyama et al. | |
| 4,986,286 A | 1/1991 | Roberts et al. | |
| 4,987,906 A | 1/1991 | Young et al. | |
| 5,005,593 A | 4/1991 | Fagg | |
| 5,019,122 A | 5/1991 | Clearman et al. | |
| 5,022,416 A | 6/1991 | Watson | |
| 5,042,510 A | 8/1991 | Curtiss et al. | |
| 5,056,537 A | 10/1991 | Brown et al. | |
| 5,060,669 A | 10/1991 | White et al. | |
| 5,060,671 A | 10/1991 | Counts et al. | |
| 5,065,775 A | 11/1991 | Fagg | |
| 5,072,744 A | 12/1991 | Luke et al. | |
| 5,074,319 A | 12/1991 | White et al. | |
| 5,076,296 A | 12/1991 | Nystrom et al. | |
| 5,093,894 A | 3/1992 | Deevi et al. | |
| 5,095,921 A | 3/1992 | Losee et al. | |
| 5,097,850 A | 3/1992 | Braunshteyn et al. | |
| 5,099,862 A | 3/1992 | White et al. | |
| 5,099,864 A | 3/1992 | Young et al. | |
| 5,103,842 A | 4/1992 | Strang et al. | |
| 5,121,757 A | 6/1992 | White et al. | |
| 5,129,409 A | 7/1992 | White et al. | |
| 5,131,415 A | 7/1992 | Munoz et al. | |
| 5,143,097 A | 9/1992 | Sohn et al. | |
| 5,144,962 A | 9/1992 | Counts et al. | |
| 5,146,934 A | 9/1992 | Deevi et al. | |
| 5,159,940 A | 11/1992 | Hayward et al. | |
| 5,159,942 A | 11/1992 | Brinkley et al. | |
| 5,179,966 A | 1/1993 | Losee et al. | |
| 5,211,684 A | 5/1993 | Shannon et al. | |
| 5,220,930 A | 6/1993 | Gentry | |
| 5,224,498 A | 7/1993 | Deevi et al. | |
| 5,228,460 A | 7/1993 | Sprinkel, Jr. et al. | |
| 5,230,354 A | 7/1993 | Smith et al. | |
| 5,235,992 A | 8/1993 | Sensabaugh | |
| 5,243,999 A | 9/1993 | Smith | |
| 5,246,018 A | 9/1993 | Deevi et al. | |
| 5,249,586 A | 10/1993 | Morgan et al. | |
| 5,261,424 A | 11/1993 | Sprinkel, Jr. | |
| 5,269,327 A | 12/1993 | Counts et al. | |
| 5,285,798 A | 2/1994 | Banerjee et al. | |
| 5,293,883 A | 3/1994 | Edwards | |
| 5,301,694 A | 4/1994 | Raymond | |
| 5,303,720 A | 4/1994 | Banerjee et al. | |
| 5,318,050 A | 6/1994 | Gonzalez-Parra et al. | |
| 5,322,075 A | 6/1994 | Deevi et al. | |
| 5,322,076 A | 6/1994 | Brinkley et al. | |
| 5,339,838 A | 8/1994 | Young et al. | |
| 5,345,951 A | 9/1994 | Serrano et al. | |
| 5,353,813 A | 10/1994 | Deevi et al. | |
| 5,357,984 A | 10/1994 | Farrier et al. | |
| 5,360,023 A | 11/1994 | Blakley et al. | |
| 5,369,723 A | 11/1994 | Counts et al. | |
| 5,372,148 A | 12/1994 | McCafferty et al. | |
| 5,377,698 A | 1/1995 | Litzinger et al. | |
| 5,388,574 A | 2/1995 | Ingebrethsen et al. | |
| 5,388,594 A | 2/1995 | Counts et al. | |
| 5,408,574 A | 4/1995 | Deevi et al. | |
| 5,435,325 A | 7/1995 | Clapp et al. | |
| 5,445,169 A | 8/1995 | Brinkley et al. | |
| 5,468,266 A | 11/1995 | Bensalem et al. | |
| 5,468,936 A | 11/1995 | Deevi et al. | |
| 5,479,948 A | 1/1996 | Counts et al. | |
| 5,498,850 A | 3/1996 | Das | |
| 5,498,855 A | 3/1996 | Deevi et al. | |
| 5,499,636 A | 3/1996 | Baggett, Jr. et al. | |
| 5,501,237 A | 3/1996 | Young et al. | |
| 5,505,214 A | 4/1996 | Collins et al. | |
| 5,515,842 A | 5/1996 | Ramseyer et al. | |
| 5,530,225 A | 6/1996 | Hajaligol | |
| 5,551,450 A | 9/1996 | Hemsley | |
| 5,551,451 A | 9/1996 | Riggs et al. | |
| 5,564,442 A | 10/1996 | MacDonald et al. | |
| 5,573,692 A | 11/1996 | Das et al. | |
| 5,591,368 A | 1/1997 | Fleischhauer et al. | |
| 5,593,792 A | 1/1997 | Farrier et al. | |
| 5,595,577 A | 1/1997 | Bensalem et al. | |
| 5,596,706 A | 1/1997 | Shimazaki et al. | |
| 5,611,360 A | 3/1997 | Tang | |
| 5,613,504 A | 3/1997 | Collins et al. | |
| 5,613,505 A | 3/1997 | Campbell et al. | |
| 5,649,552 A | 7/1997 | Cho et al. | |
| 5,649,554 A | 7/1997 | Sprinkel et al. | |
| 5,659,656 A | 8/1997 | Das | |
| 5,665,262 A | 9/1997 | Hajaligol et al. | |
| 5,666,976 A | 9/1997 | Adams et al. | |
| 5,666,977 A | 9/1997 | Higgins et al. | |
| 5,666,978 A | 9/1997 | Counts et al. | |
| 5,687,746 A | 11/1997 | Rose et al. | |
| 5,692,525 A | 12/1997 | Counts et al. | |
| 5,692,526 A | 12/1997 | Adams et al. | |
| 5,708,258 A | 1/1998 | Counts et al. | |
| 5,711,320 A | 1/1998 | Martin | |
| 5,726,421 A | 3/1998 | Fleischhauer et al. | |
| 5,727,571 A | 3/1998 | Meiring et al. | |
| 5,730,158 A | 3/1998 | Collins et al. | |

(56) References Cited

U.S. PATENT DOCUMENTS

| | | |
|---|---|---|
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |
| 5,829,453 A | 11/1998 | White et al. |
| 5,865,185 A | 2/1999 | Collins et al. |
| 5,865,186 A | 2/1999 | Volsey, II |
| 5,878,752 A | 3/1999 | Adams et al. |
| 5,880,439 A | 3/1999 | Deevi et al. |
| 5,894,841 A | 4/1999 | Voges |
| 5,915,387 A | 6/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,033,623 A | 3/2000 | Deevi et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,855 A | 10/2000 | Nevett et al. |
| 6,125,866 A | 10/2000 | Nichols et al. |
| 6,155,268 A | 12/2000 | Takeuchi |
| 6,164,287 A | 12/2000 | White |
| 6,182,670 B1 | 2/2001 | White |
| 6,196,218 B1 | 3/2001 | Voges |
| 6,196,219 B1 | 3/2001 | Hess et al. |
| 6,216,706 B1 | 4/2001 | Kumar et al. |
| 6,289,898 B1 | 9/2001 | Fournier et al. |
| 6,349,728 B1 | 2/2002 | Pham |
| 6,357,671 B1 | 3/2002 | Cewers |
| 6,418,938 B1 | 7/2002 | Fleischhauer et al. |
| 6,446,426 B1 | 9/2002 | Sweeney et al. |
| 6,532,965 B1 | 3/2003 | Abhulimen et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,701,936 B2 | 3/2004 | Shafer et al. |
| 6,715,494 B1 | 4/2004 | McCoy |
| 6,730,832 B1 | 5/2004 | Dominguez et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,810,883 B2 | 11/2004 | Felter et al. |
| 6,854,461 B2 | 2/2005 | Nichols |
| 6,854,470 B1 | 2/2005 | Pu |
| 6,994,096 B2 | 2/2006 | Rostami et al. |
| 7,011,096 B2 | 3/2006 | Li et al. |
| 7,017,585 B2 | 3/2006 | Li et al. |
| 7,025,066 B2 | 4/2006 | Lawson et al. |
| 7,117,867 B2 | 10/2006 | Cox et al. |
| 7,163,015 B2 | 1/2007 | Moffitt |
| 7,173,222 B2 | 2/2007 | Cox et al. |
| 7,185,659 B2 | 3/2007 | Sharpe et al. |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,513,253 B2 | 4/2009 | Kobayashi et al. |
| 7,647,932 B2 | 1/2010 | Cantrell et al. |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,878,209 B2 | 2/2011 | Newbery et al. |
| 7,896,002 B2 * | 3/2011 | Watanabe ......... A61M 15/0065 128/200.14 |
| 7,896,006 B2 | 3/2011 | Hamano et al. |
| 8,066,010 B2 | 11/2011 | Newbery et al. |
| 8,079,371 B2 | 12/2011 | Robinson et al. |
| 8,127,772 B2 | 3/2012 | Montaser |
| 8,156,944 B2 | 4/2012 | Han |
| 8,314,591 B2 | 11/2012 | Terry et al. |
| 8,365,742 B2 | 2/2013 | Hon |
| 8,375,957 B2 | 2/2013 | Hon |
| 8,393,331 B2 | 3/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0131859 A1 | 7/2003 | Li et al. |
| 2003/0226837 A1 | 12/2003 | Blake et al. |
| 2004/0020500 A1 | 2/2004 | Wrenn et al. |
| 2004/0118401 A1 | 6/2004 | Smith et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0226568 A1 | 11/2004 | Takeuchi et al. |
| 2004/0255965 A1 | 12/2004 | Perfetti et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0172976 A1 | 8/2005 | Newman et al. |
| 2005/0268911 A1 | 12/2005 | Cross et al. |
| 2005/0274390 A1 | 12/2005 | Banerjee et al. |
| 2006/0016453 A1 | 1/2006 | Kim |
| 2006/0070633 A1 | 4/2006 | Rostami et al. |
| 2006/0162733 A1 | 7/2006 | McGrath et al. |
| 2006/0185687 A1 | 8/2006 | Hearn et al. |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Han |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0320863 A1 | 12/2009 | Fernando et al. |
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0250280 A1 * | 9/2010 | Sutherland ........ A61M 15/0065 705/3 |
| 2010/0258139 A1 | 10/2010 | Onishi et al. |
| 2010/0300467 A1 | 12/2010 | Kuistila et al. |
| 2010/0307518 A1 | 12/2010 | Wang |
| 2010/0313901 A1 * | 12/2010 | Fernando .............. A24F 47/008 131/330 |
| 2011/0005535 A1 | 1/2011 | Xiu |
| 2011/0011396 A1 | 1/2011 | Fang |
| 2011/0036363 A1 | 2/2011 | Urtsev et al. |

(56) References Cited

U.S. PATENT DOCUMENTS

| | | |
|---|---|---|
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120482 A1 | 5/2011 | Brenneise |
| 2011/0126847 A1 | 6/2011 | El-Shall et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0180082 A1 | 7/2011 | Banerjee et al. |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0220315 A1* | 8/2013 | Conley ............... A61M 11/042 128/202.21 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |

FOREIGN PATENT DOCUMENTS

| | | |
|---|---|---|
| CA | 2641869 A1 | 5/2010 |
| CA | 2 752 255 | 8/2010 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 468 116 | 6/2012 |
| GB | 1444461 | 7/1976 |
| GB | 2469850 | 11/2010 |
| WO | WO 86/02528 | 5/1986 |
| WO | WO 97/48293 | 12/1997 |
| WO | WO 02/37990 | 5/2002 |
| WO | WO 2004/043175 | 5/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO 2011/081558 | 7/2011 |
| WO | WO 2012/072762 | 6/2012 |
| WO | WO 2012/100523 | 8/2012 |
| WO | WO 2013/089551 | 6/2013 |
| WO | 2013102612 A2 | 7/2013 |

OTHER PUBLICATIONS

International Preliminary Report on Patentability dated Jun. 28, 2016 in PCT/US2015/019879.

* cited by examiner

AEROSOL DELIVERY SYSTEM AND RELATED METHOD, APPARATUS, AND COMPUTER PROGRAM PRODUCT FOR PROVIDING CONTROL INFORMATION TO AN AEROSOL DELIVERY DEVICE VIA A CARTRIDGE

FIELD OF THE DISCLOSURE

The present disclosure relates to aerosol delivery devices such as smoking articles, and more particularly to an aerosol delivery system and methods, apparatuses, and computer program products for providing control information to an aerosol delivery device via a cartridge. The smoking articles may be configured to heat a material, which may be made or derived from tobacco or otherwise incorporate tobacco, to form an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. U.S. App. Pub. No. 2013/0255702 to Griffith, Jr. et al., U.S. Pat. App. Pub. No. 2014/0000638 to Sebastian et al., U.S. Pat. App. Pub. No. 2014/0060554 to Collett et al., and U.S. patent application Ser. No. 13/647,000, filed Oct. 8, 2012, which are incorporated herein by reference.

Ongoing developments in the field of aerosol delivery devices have resulted in increasingly sophisticated aerosol delivery devices. For example, many aerosol delivery devices include a processor, microcontroller, or the like which may be configured to execute control software for controlling operation of the device. The use of such control software has enabled the implementation of increasingly sophisticated features on aerosol delivery devices. However, updating control software and adjusting software controlled configuration settings on an aerosol delivery device continues to be problematic.

SUMMARY OF THE DISCLOSURE

The present disclosure relates to an aerosol delivery system and methods, apparatuses, and computer program products for providing control information to an aerosol delivery device via a cartridge. For example, in one aspect, an aerosol delivery system is provided. The aerosol delivery system may include a control body for an aerosol delivery device. The control body may include a processing circuitry. The aerosol delivery system may further include a cartridge carrying control information that is readable by the processing circuitry. The control body may be configured to removably engage the cartridge. The processing circuitry may be configured to at least read the control information carried by the cartridge when the control body and cartridge are engaged; and perform an action abased at least in part on the control information.

In another aspect, a control body for an aerosol delivery device is provided. The control body may include a cartridge engaging portion configured to removably engage a cartridge. The control body may further include processing circuitry, which may be configured to at least read control information carried by the cartridge when the cartridge is engaged with the control body; and perform an action based at least in part on the control information.

In a further aspect, a cartridge configured for use with an aerosol delivery device is provided. The cartridge may comprise a control body engaging portion configured to removably engage a control body of the aerosol delivery device. The cartridge may be configured to carry control information readable by the control body when the control body and cartridge are engaged. The control information may be configured to cause the control body to perform an action.

In an additional aspect, a method for providing control information to an aerosol delivery device is provided. The method may include a control body for the aerosol delivery device reading control information carried by a cartridge removably engaged with the control body; and performing an action based at least in part on the control information.

In still a further aspect, a computer program product is provided, which may include at least one non-transitory computer-readable storage medium having program instructions stored thereon. When executed by at least one processor implemented on a control body for an aerosol delivery device, the stored program instructions may cause the at least one processor to perform a method comprising reading control information carried by a cartridge removably engaged with the control body; and performing an action based at least in part on the control information.

This Summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages will become apparent from the following detailed description taken in conjunction with the accompanying drawings which illustrate, by way of example, the principles of some described embodiments.

BRIEF DESCRIPTION OF THE FIGURES

Figure 1:
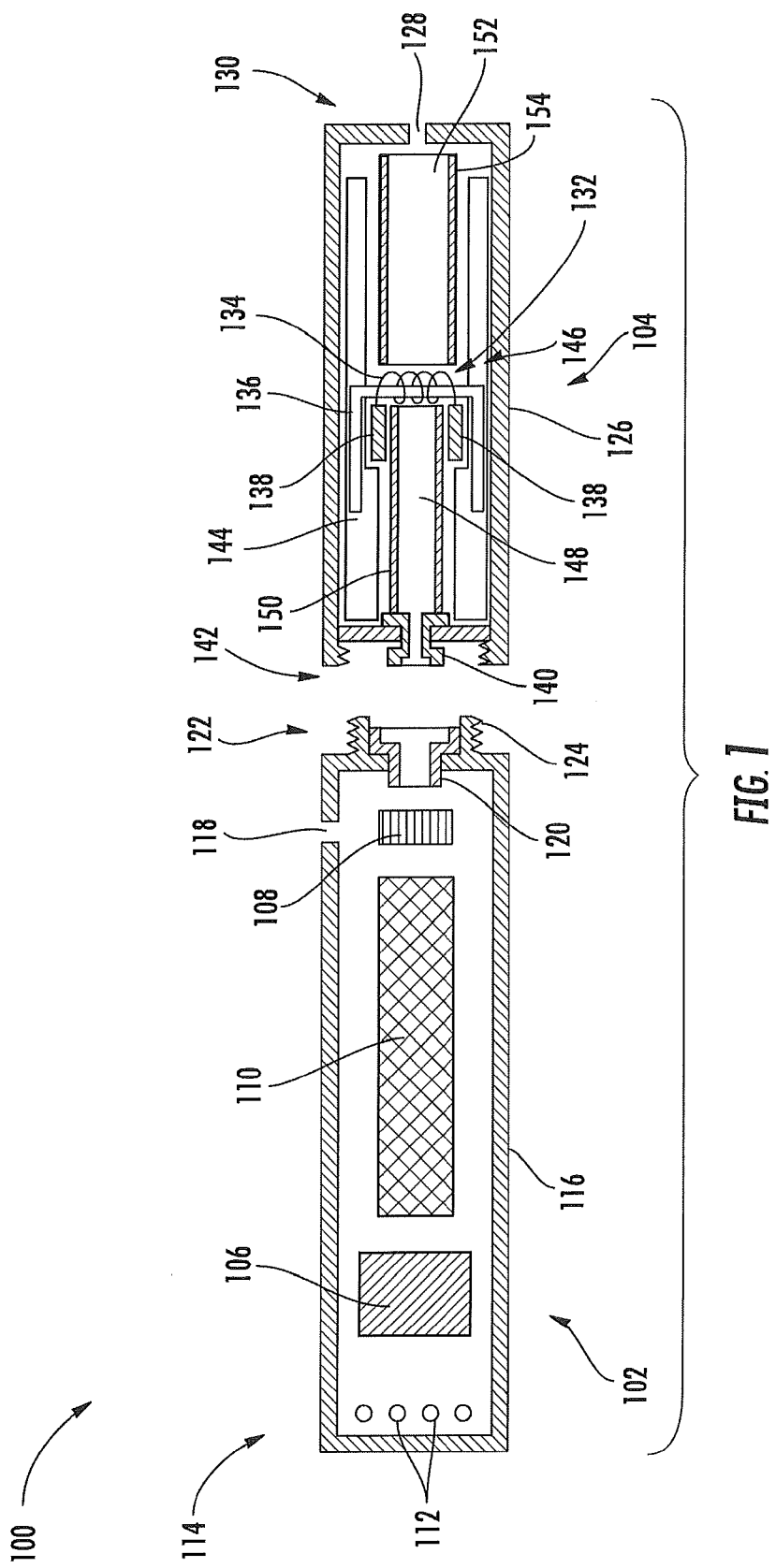
Figure 2:
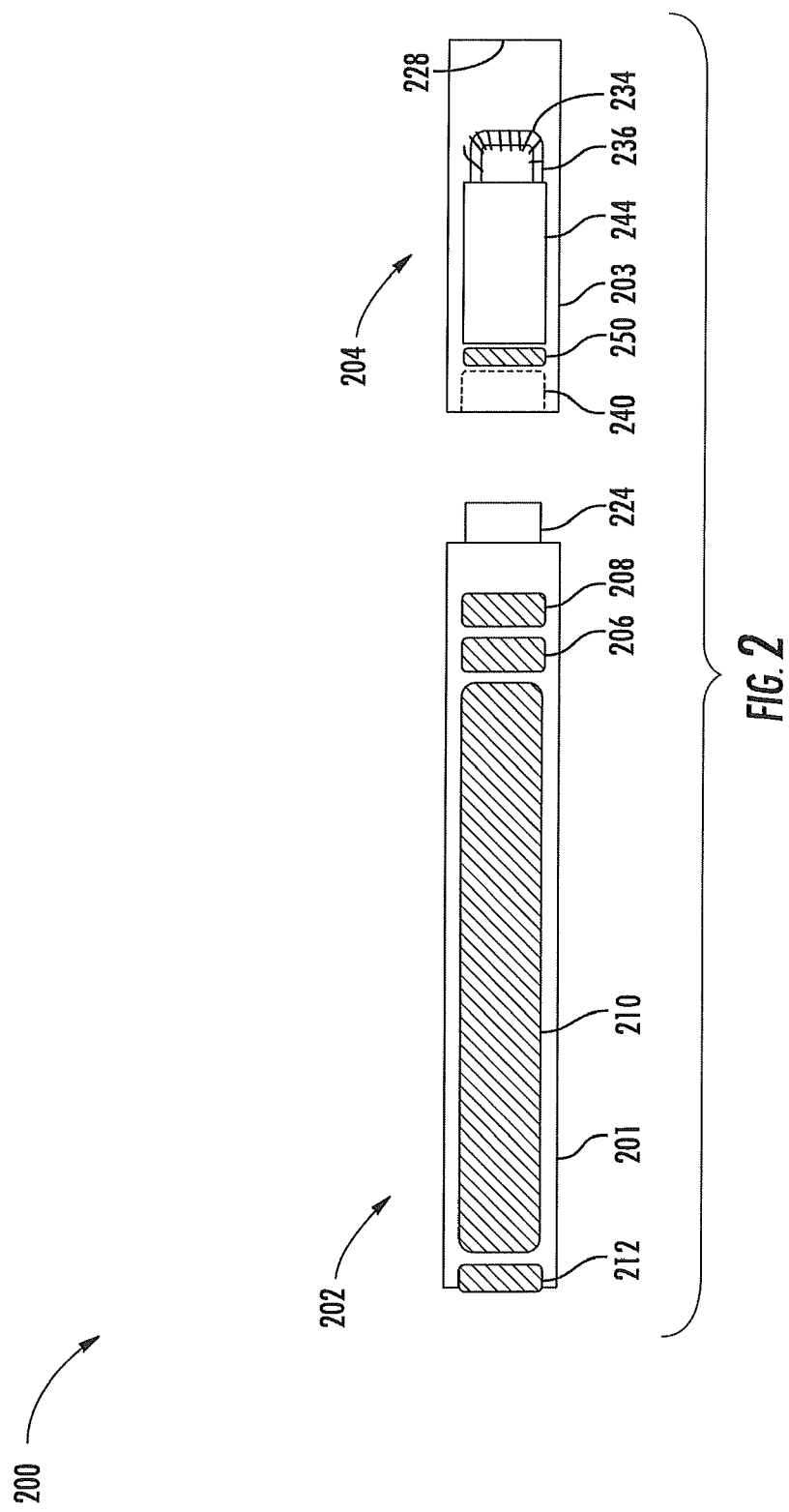
Figure 3:
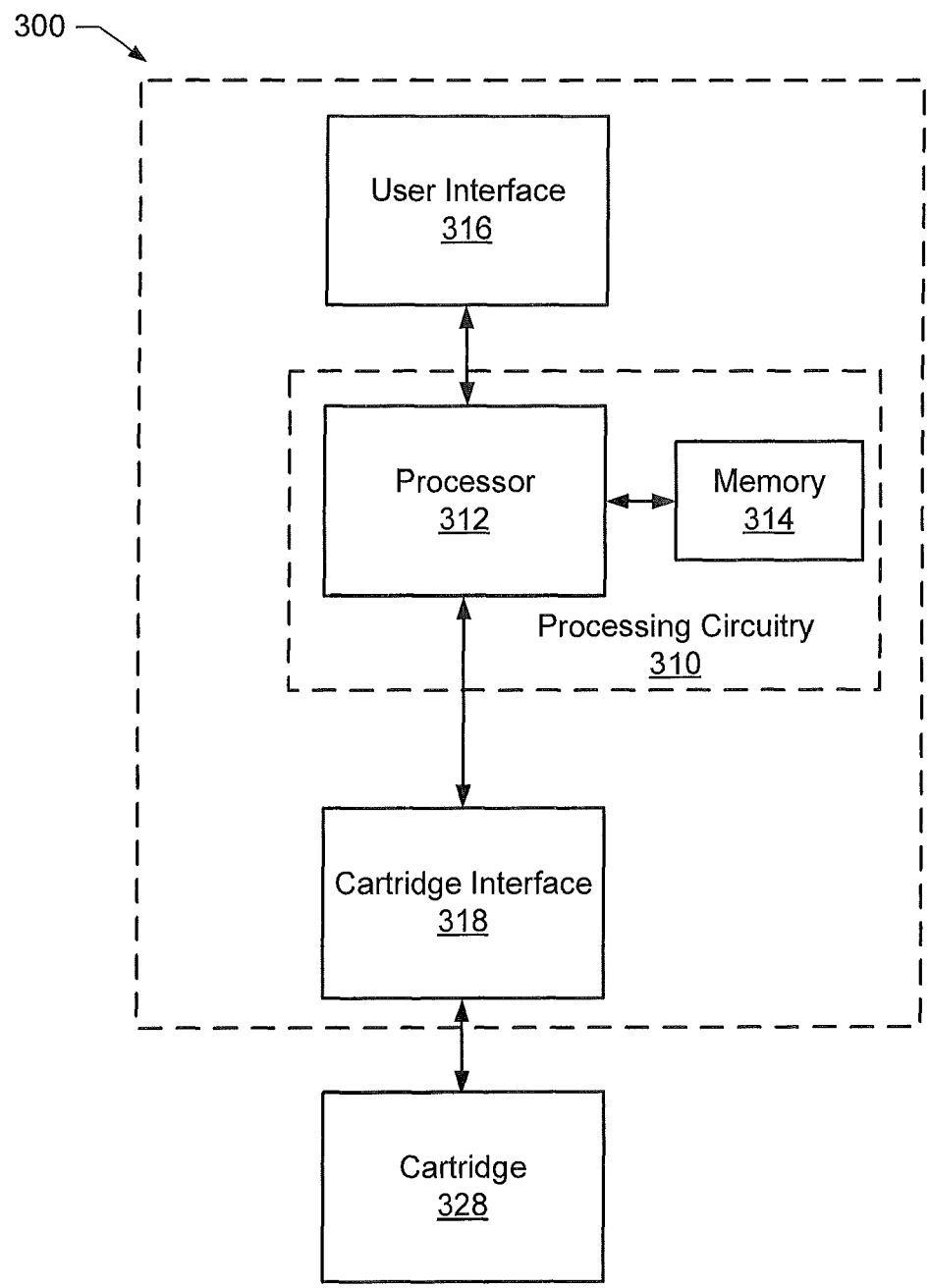
Figure 4:
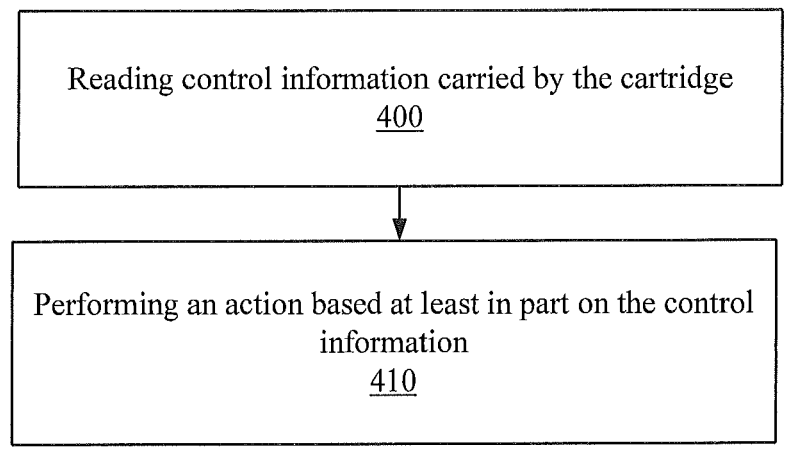
Figure 5:
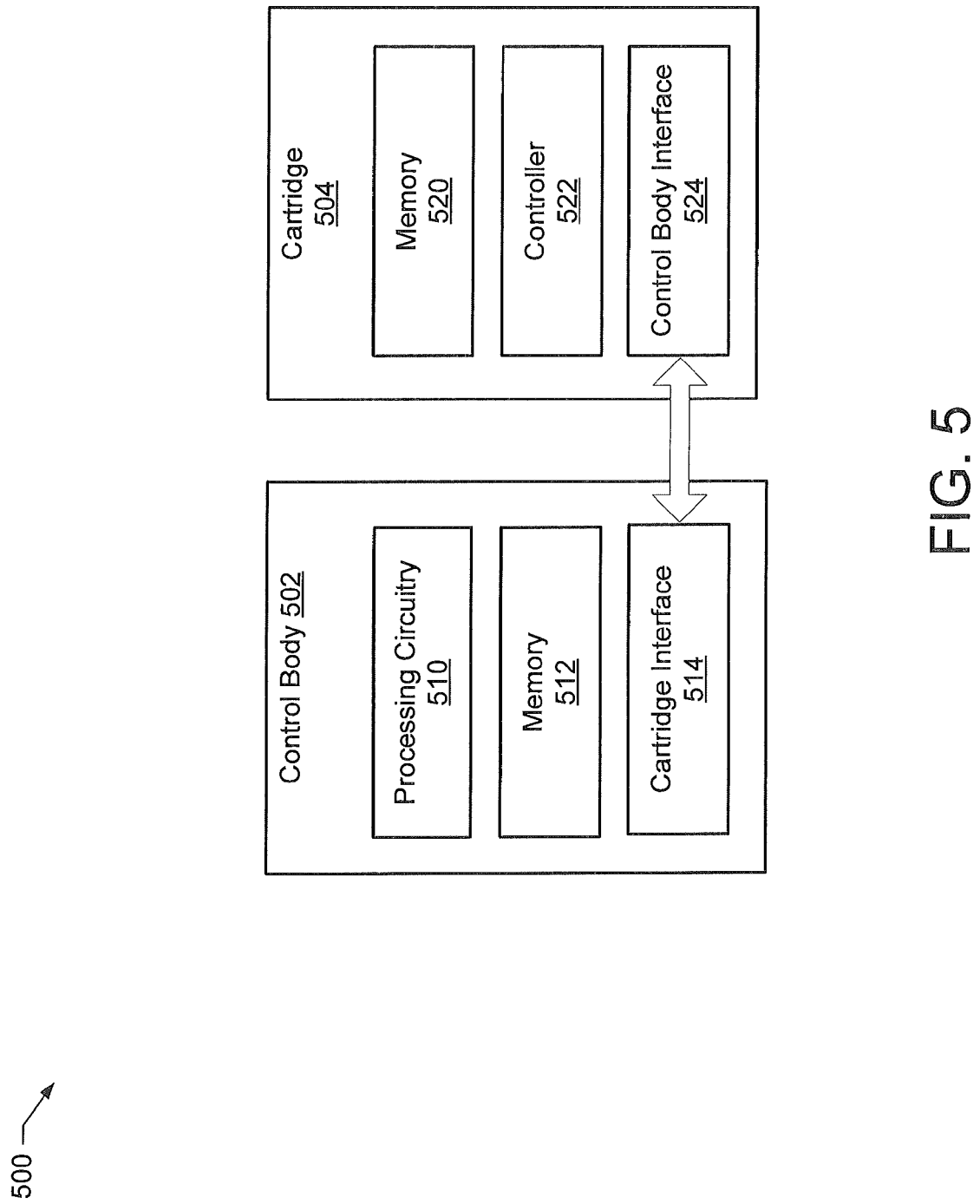
Figure 6:
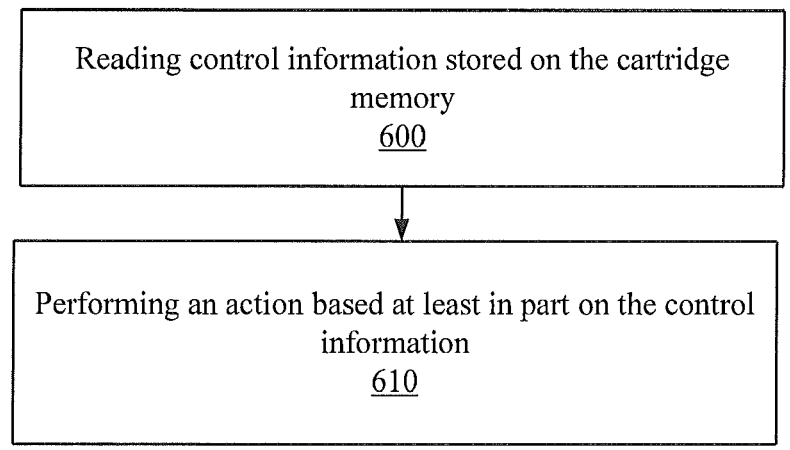
Figure 7:
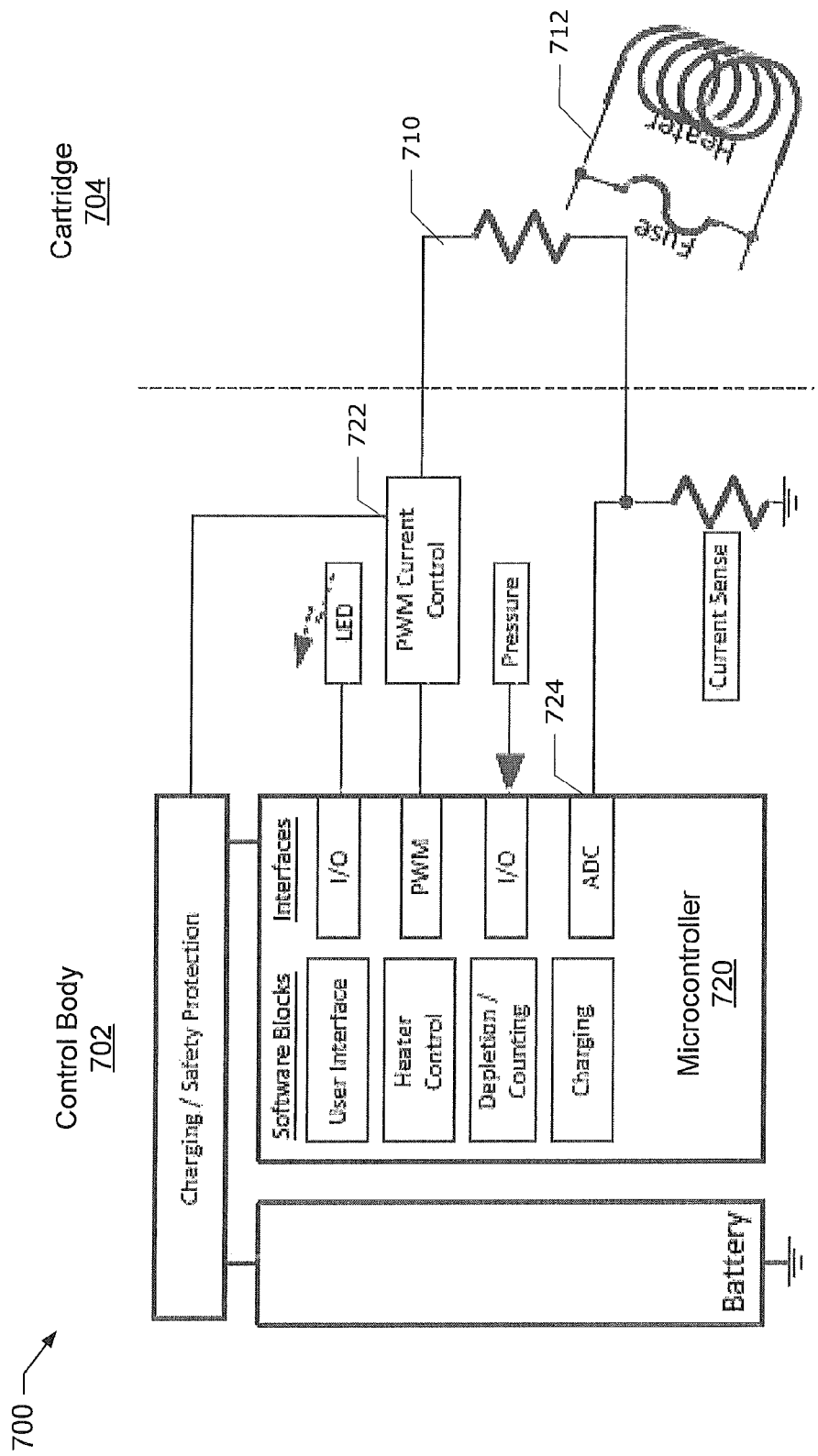
Figure 8:
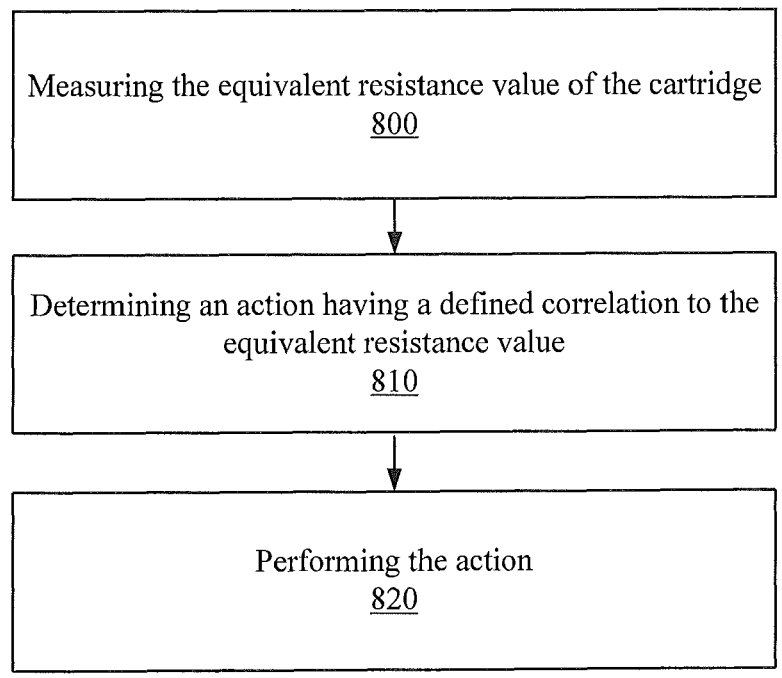

Having thus described the disclosure in the foregoing general terms, reference will now be made to the accompanying drawings, which are not necessarily drawn to scale, and wherein:

FIG. 1 is a sectional view through an electronic smoking article comprising a control body and a cartridge according to an example embodiment of the present disclosure;

FIG. 2 is a sectional view through an electronic smoking article comprising a cartridge and a control body and including a reservoir housing according to an example embodiment of the present disclosure;

FIG. 3 illustrates a block diagram of an apparatus that may be implemented on a control body and interfaced with a cartridge in accordance with some example embodiments of the present disclosure;

FIG. 4 illustrates a flowchart according to an example method for providing control information to an aerosol delivery device via a cartridge in accordance with some example embodiments of the present disclosure;

FIG. 5 illustrates an example aerosol delivery system comprising a control body and a cartridge carrying control information stored on a memory in accordance with some example embodiments of the present disclosure;

FIG. 6 illustrates a flowchart according to an example method for providing control information to an aerosol delivery device via a cartridge carrying control information stored on a memory in accordance with some example embodiments of the present disclosure;

FIG. 7 illustrates an example aerosol delivery system comprising a control body and a cartridge carrying control information in the form of an equivalent resistance value in accordance with some example embodiments of the present disclosure; and FIG. 8 illustrates a flowchart according to an example method for providing control information to an aerosol delivery device via a cartridge carrying control information in the form of an equivalent resistance value in accordance with some example embodiments of the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Some example embodiments of the present disclosure relate to an aerosol delivery system and methods, apparatuses, and computer program products for providing control information to an aerosol delivery device via a cartridge. Aerosol delivery devices (e.g., smoking articles) that may be used with various example embodiments may, by way of non-limiting example, include so-called "e-cigarettes." It should be understood that the mechanisms, components, features, and methods associated with such aerosol delivery devices may be embodied in many different forms and associated with a variety of articles.

In this regard, the present disclosure provides descriptions of aerosol delivery devices that use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco.

Aerosol delivery devices of the present disclosure also can be characterized as being vapor-producing articles, smoking articles, or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising an outer body or shell containing one or more reusable components (e.g., a rechargeable battery and various electronics for controlling the operation of that article), and at the other end and removably attached thereto an outer body or shell containing a disposable portion (e.g., a disposable flavor-containing cartridge). In this regard, the control body and disposable portion (e.g., cartridge) of such example embodiments may be removably engaged via respective engaging portions to form a functional aerosol delivery device. More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices, such as those representative products listed in the background art section of the present disclosure.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety.

Alignment of the components within the aerosol delivery device can vary. In specific embodiments, the aerosol precursor composition can be located near an end of the article (e.g., within a cartridge, which in certain circumstances can be replaceable and disposable), which may be proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices, such as those representative products listed in the background art section of the present disclosure.

An aerosol delivery device incorporates a battery or other electrical power source to provide current flow sufficient to provide various functionalities to the article, such as resistive heating, powering of control systems, powering of indicators, and the like. The power source can take on various embodiments. Preferably, the power source is able to deliver sufficient power to rapidly heat the heating member to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

One example embodiment of an aerosol delivery device 100 that may be used with various embodiments is provided in FIG. 1. As seen in the cross-section illustrated therein, the aerosol delivery device 100 can comprise a control body 102 and a cartridge 104 that can be permanently or detachably aligned in a functioning relationship. In this regard, the control body 102 may include a cartridge engaging portion and the cartridge 104 may include a control body engaging portion to support engagement of the control body 102 and cartridge 104 such that the control body 102 and cartridge 104 may be aligned in a functioning relationship. For example, a cartridge engaging portion of the control body 102 may be provided by one or more aspects the coupler 120, the proximal attachment end 122, and/or control body projection 124, as described further below. The control body engaging portion of the cartridge 104 may, for example, be provided by one or more aspects of the plug 140 and/or a distal attachment end 142, as described further below. Although a threaded engagement of the control body 102 and cartridge 104 is illustrated in FIG. 1, it is understood that further means of engagement may be employed, such as a press-fit engagement, interference fit, a magnetic engagement, or the like.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (e.g., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264, filed Mar. 15, 2013, which is incorporated herein by reference in its entirety. It will be appreciated that embodiments including a rechargeable battery may include any type of rechargeable battery, such as by way of non-limiting example, a lithium ion battery (e.g., a rechargeable lithium-manganese dioxide battery), lithium ion polymer battery, nickel-zinc battery, nickel-metal hydride battery, nickel cadmium battery, rechargeable alkaline battery, some combination thereof, and/or other type of rechargeable battery. Further, in some embodiments the cartridge may comprise a single-use cartridge, as disclosed in U.S. Pat. App. Pub. No. 2014/0060555 to Chang et al., which is incorporated herein by reference in its entirety.

In the exemplified embodiment, the control body 102 includes a control component 106 (e.g., a microcontroller), a flow sensor 108, and a battery 110, which can be variably aligned, and can include a plurality of indicators 112 at a distal end 114 of an outer body 116. The indicators 112 can be provided in varying numbers and can take on different shapes and can even be an opening in the body (such as for release of sound when such indicators are present). In the exemplified embodiment, a haptic feedback component 101 is included with the control component 106. As such, the haptic feedback component may be integrated with one or more components of a smoking article for providing vibration or like tactile indication of use or status to a user. See, for example, the disclosure of U.S. patent application Ser. No. 13/946,309, filed Jul. 19, 2013, which is incorporated herein by reference in its entirety.

An air intake 118 may be positioned in the outer body 116 of the control body 102. A coupler 120 also is included at the proximal attachment end 122 of the control body 102 and may extend into a control body projection 124 to allow for ease of electrical connection with an atomizer or a component thereof, such as a resistive heating element (described below) when the cartridge 104 is attached to the control body. Although the air intake 118 is illustrated as being provided in the outer body 116, in another embodiment the air intake may be provided in a coupler as described, for example, in U.S. patent application Ser. No. 13/841,233; Filed Mar. 15, 2013.

The cartridge 104 includes an outer body 126 with a mouth opening 128 at a mouthend 130 thereof to allow passage of air and entrained vapor (i.e., the components of the aerosol precursor composition in an inhalable form) from the cartridge to a consumer during draw on the aerosol delivery device 100. The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, or the like.

The cartridge 104 further includes an atomizer 132 comprising a resistive heating element 134 (e.g., a wire coil) configured to produce heat and a liquid transport element 136 (e.g., a wick) configured to transport a liquid. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), and ceramic (e.g., a positive temperature coefficient ceramic). Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the coupler 120 to form an electrical connection such that current controllably flows from the battery 110, through the coupler and plug, and to the heating element 134. The outer body 126 of the cartridge 104 can continue across the distal attachment end 142 such that this end of the cartridge is substantially closed with the plug 140 protruding therefrom.

A liquid transport element can be combined with a reservoir to transport an aerosol precursor composition to an aerosolization zone. In the embodiment shown in FIG. 1, the cartridge 104 includes a reservoir layer 144 comprising layers of nonwoven fibers formed into the shape of a tube encircling the interior of the outer body 126 of the cartridge, in this embodiment. An aerosol precursor composition is retained in the reservoir layer 144. Liquid components, for example, can be sorptively retained by the reservoir layer 144. The reservoir layer 144 is in fluid connection with a liquid transport element 136. The liquid transport element 136 transports the aerosol precursor composition stored in the reservoir layer 144 via capillary action to an aerosolization zone 146 of the cartridge 104. As illustrated, the liquid transport element 136 is in direct contact with the heating element 134 that is in the form of a metal wire coil in this embodiment.

It is understood that an aerosol delivery device that can be manufactured according to the present disclosure can encompass a variety of combinations of components useful in forming an electronic aerosol delivery device. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety. Further, U.S. Pat. App. Pub. No. 2014/0060554 to Collett et al., discloses an electronic smoking article including a microheater, and which is incorporated herein by reference in its entirety.

Reference also is made to U.S. Pat. Pub. No. 2013/0213419, which discloses a ribbon of electrically resistive mesh material that may be wound around a wick, and to U.S. Pat. Pub. No. 2013/0192619, which discloses a heater coil about a wick wherein the coil windings have substantially uniform spacing between each winding. In certain embodiments according to the present disclosure, a heater may comprise a metal wire, which may be wound with a varying pitch around a liquid transport element, such as a wick. An exemplary variable pitch heater than may be used according to the present disclosure is described in U.S. patent application Ser. No. 13/827,994, filed Mar. 14, 2013, the disclosure of which is incorporated herein by reference in its entirety.

Reference also is made to a liquid supply reservoir formed of an elastomeric material and adapted to be manually compressed so as to pump liquid material therefrom, as disclosed in U.S. Pat. Pub. No. 2013/0213418. In certain embodiments according to the present disclosure, a reservoir may particularly be formed of a fibrous material, such as a fibrous mat or tube that may absorb or adsorb a liquid material.

In another embodiment substantially the entirety of the cartridge may be formed from one or more carbon materials, which may provide advantages in terms of biodegradability and absence of wires. In this regard, the heating element may comprise a carbon foam, the reservoir may comprise carbonized fabric, and graphite may be employed to form an electrical connection with the battery and controller. Such carbon cartridge may be combined with one or more elements as described herein for providing illumination of the cartridge in some embodiments. An example embodiment of a carbon-based cartridge is provided in U.S. Pat. App. Pub. No. 2013/0255702 to Griffith, Jr. et al., which is incorporated herein by reference in its entirety.

In use, when a user draws on the article 100, the heating element 134 is activated (e.g., such as via a flow sensor), and the components for the aerosol precursor composition are vaporized in the aerosolization zone 146. Drawing upon the mouthend 130 of the article 100 causes ambient air to enter the air intake 118 and pass through the central opening in the coupler 120 and the central opening in the plug 140. In the cartridge 104, the drawn air passes through an air passage 148 in an air passage tube 150 and combines with the formed vapor in the aerosolization zone 146 to form an aerosol. The aerosol is whisked away from the aerosolization zone 146, passes through an air passage 152 in an air passage tube 154, and out the mouth opening 128 in the mouthend 130 of the article 100.

The various components of an aerosol delivery device according to the present disclosure can be chosen from components described in the art and commercially available.

Examples of batteries that can be used according to the disclosure are described in U.S. Pat. App. Pub. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

Reference also is made to International Publications WO 2013/098396, WO 2013/098397, and WO 2013/098398, which describe controllers configured to control power supplied to a heater element from a power source as a means to monitor a status of the device, such as heater temperature, air flow past a heater, and presence of an aerosol forming material near a heater. In particular embodiments, the present disclosure provides a variety of control systems adapted to monitor status indicators, such as through communication of a microcontroller in a control body and a microcontroller or other electronic component in a cartridge component.

The aerosol precursor, which may also be referred to as an aerosol precursor composition or a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

Still further components can be utilized in the aerosol delivery device of the present disclosure. For example, U.S. Pat. No. 5,154,192 to Sprinkel et al. discloses indicators that may be used with smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,388,574 to Ingebrethsen; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. No. 8,365,742 to Hon; U.S. Pat. No. 8,375,957 to Hon; U.S. Pat. No. 8,393,331 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; U.S. patent application Ser. No. 13/841,233, filed Mar. 15, 2013; and U.S. patent application Ser. No. 14/170,838, filed Feb. 3, 2014, each of which is incorporated herein by reference in its entirety. A variety of the materials disclosed by the foregoing documents may be incorporated into the present devices in various embodiments, and all of the foregoing disclosures are incorporated herein by reference in their entireties.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

A further exemplary embodiment of a smoking article 200 (e.g., an aerosol delivery device) including a reservoir housing 244 that may be used with various embodiments according to the present disclosure is shown in FIG. 2. As illustrated therein, a control body 202 can be formed of a control body shell 201 that can include a control component 206, a flow sensor 208, a battery 210, and an LED 212. A cartridge 204 can be formed of a cartridge shell 203 enclosing the reservoir housing 244 that is in fluid communication with a liquid transport element 236 adapted to wick or otherwise transport an aerosol precursor composition stored in the reservoir housing to a heater 234. An opening 228 may be present in the cartridge shell 203 to allow for egress of formed aerosol from the cartridge 204. Such components are representative of the components that may be present in a cartridge and are not intended to limit the scope of cartridge components that are encompassed by the present disclosure. The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. In this regard, the control body projection 224 may provide a cartridge engaging portion, while the cartridge receptacle 240 may provide a control body engaging portion to enable a functional engagement between the control body 202 and cartridge 204. The cartridge 204 also may include one or more electronic components 250, which may include an IC, a memory component, a sensor, or the like. The electronic component 250 may be adapted to communicate with the control component 206.

In some embodiments, an electronic smoking article can comprise a hollow shell that is adapted to enclose one or more further elements of the device. The hollow shell may be a single unitary piece that includes all elements of the electronic smoking article. In two piece embodiments, such as described above, the hollow shell may relate to a cartridge shell or a control body shell.

Having described several example embodiments of aerosol delivery devices that may be used with various example embodiments, several embodiments of an aerosol delivery system and methods, apparatuses, and computer program products for providing control information to an aerosol delivery device via a cartridge will now be described. In this regard, some example embodiments relate to an aerosol delivery system comprising a control body for an aerosol delivery device and a cartridge. The cartridge of such example embodiments may carry control information that is readable by the control body (e.g., by processing circuitry of the control body) when the control body and cartridge are engaged. The control body (e.g., processing circuitry of the control body) may be configured to perform an action based at least in part on the control information. For example, the control information may be used to update a configuration setting of an aerosol delivery device, perform a software update on the aerosol delivery device, run a diagnostic program on the aerosol delivery device, and/or the like. Accordingly, a cartridge in accordance with such embodiments may be used to provide an interface to control software of the aerosol delivery device so as to perform various control options for updating and/or testing functionality of the aerosol delivery device.

FIG. 3 illustrates a block diagram of an apparatus 300 that may be implemented on a control body, such as control body 102 and/or control body 202, and interfaced with a cartridge 328 in accordance with some example embodiments of the present disclosure. It will be appreciated that the components, devices or elements illustrated in and described with respect to FIG. 3 below may not be mandatory and thus some may be omitted in certain embodiments. Additionally, some embodiments may include further or different components, devices or elements beyond those illustrated in and described with respect to FIG. 3.

In some example embodiments, the apparatus 300 may include processing circuitry 310 that is configurable to perform and/or control performance of functions of a control body for an aerosol delivery device in accordance with one or more example embodiments disclosed herein. Thus, the processing circuitry 310 may be configured to perform data processing, application execution and/or other processing and management services that may be implemented to perform functionality of the control body according to one or more example embodiments.

In some embodiments, the apparatus 300 or a portion(s) or component(s) thereof, such as the processing circuitry 310, may include one or more chipsets, which may each include one or more chips. The processing circuitry 310 and/or one or more further components of the apparatus 300 may therefore, in some instances, be configured to implement an embodiment on a chipset. A chipset in accordance with such example embodiments may be implemented on a control body of an aerosol delivery device.

The processing circuitry 310 may, for example, comprise an embodiment of control component 106, and/or control component 206. In some example embodiments, the processing circuitry 310 may include a processor 312 and, in some embodiments, such as that illustrated in FIG. 3, may further include a memory 314. The processing circuitry 310 may be in communication with or otherwise control a user interface 316 and/or cartridge interface 318.

The processor 312 may be embodied in a variety of forms. For example, the processor 312 may be embodied as various hardware-based processing means such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 312 may comprise a plurality of processors. The plurality of processors may be in operative communication with each other and may be collectively configured to perform one or more functionalities of a control body on which the apparatus 300 may be implemented. In some example embodiments, the processor 312 may be configured to execute instructions that may be stored in the memory 314 and/or that may be otherwise accessible to the processor 312. As such, whether configured by hardware or by a combination of hardware and software, the processor 312 may be capable of performing operations according to various embodiments while configured accordingly.

In some example embodiments, the memory 314 may include one or more memory devices. Memory 314 may include fixed and/or removable memory devices. In some embodiments, the memory 314 may provide a non-transitory computer-readable storage medium that may store computer program instructions that may be executed by the processor 312. In this regard, the memory 314 may be configured to store information, data, applications, instructions and/or the like for enabling the apparatus 300 to carry out various functions of a control body in accordance with one or more example embodiments. For example, in some embodiments, memory 314 may be configured to store control software, configuration settings, and/or other data, programs, and/or the like that may be used to control operation of an aerosol delivery device. In some embodiments, the memory 314 may be in communication with one or more of the processor 312, user interface 316, or cartridge interface 318 via a bus (or buses) for passing information among components of the apparatus 300.

In some example embodiments, the apparatus 300 may further include the user interface 316. The user interface 316 may be in communication with the processing circuitry 310 to receive an indication of a user input and/or to provide an audible, visual, mechanical, or other output to a user. For example, the user interface 316 may include one or more buttons, keys, and/or other input mechanisms to enable a user to control operation of an aerosol delivery device. For example, the user interface 316 may provide an input mechanism(s) to enable a user to power an aerosol delivery device on/off, to activate a heating element to generate a vapor or aerosol for inhalation, and/or to otherwise actuate and/or control functionality of an aerosol delivery device. As a further example, the user interface 316 may provide one or more indicator lights, such as one or more LEDs (e.g., LED 212), a display, a speaker, and/or other output mechanism that may be used to indicate an operating status of an aerosol delivery device, a charge level of a battery, an amount of aerosol precursor composition remaining in a cartridge that may be engaged with the control body, and/or to provide other status information that may be related to operation of an aerosol delivery device to a user. In some example embodiments, the user interface 316 may include a vibrator and/or other haptic feedback device (e.g., haptic feedback component 101), which may impart a vibration and/or other motion on the aerosol delivery device, such as to provide feedback in response to a user input, provide a status notification (e.g., a status related to a remaining battery charge level, a status related to a level of aerosol precursor composition in a cartridge, and/or other status notification that may be provided), and/or to provide other feedback or notification to a user.

The apparatus 300 may further include a cartridge interface 318, which may be configured to support communication and/or other interaction between the processing circuitry 310 and/or other element of a control body and a cartridge 328, which may be removably engaged with a control body on which the apparatus 300 may be implemented. In this regard, the cartridge interface 318 may comprise any interface that may enable the processing circuitry 310 to read control information that may be carried by the cartridge 328 in accordance with various example embodiments.

For example, in some embodiments, the cartridge interface 318 may comprise a communication or data interface enabling data communication between the processing circuitry 310 and cartridge 328. In some such example embodiments, the cartridge interface 318 may, for example, comprise a wireline communication interface, such as a serial communication interface, universal serial bus (USB) interface, FireWire interface, and/or other wireline communication interface that may be used to communicate data between two entities. Additionally or alternatively, in some embodiments in which the cartridge interface 318 may comprise a communication or data interface, the cartridge interface 318 may provide a wireless communication interface, which may be configured to use a wireless communications technology, such as Wi-Fi and/or other IEEE 802.11 technology, Bluetooth, Zigbee, wireless USB, near field communication (NFC), radio frequency identification (RFID), and/or other wireless communications technology that may be used to convey data from one entity (e.g., the cartridge 328) to another (e.g., to the processing circuitry 310 and/or other element that may be implemented on a control body for an aerosol delivery device).

Additionally or alternatively, in some example embodiments, the cartridge interface 318 may comprise an interface that may be used to provide power to and/or otherwise control a cartridge, such as to control a heating element that may be used to heat aerosol precursor composition to generate an inhalable substance. For example, the cartridge interface 318 of some such example embodiments may comprise one or more heater connection points that may be configured to read current sensing data for a cartridge and/or to switch power to a heater element of a cartridge. In some such example embodiments, a heater connection point(s) may be repurposed to provide a serial interface, which may be used to convey data between the cartridge 328 and the processing circuitry 310 and/or other element of a control body. For example, an input that may be configured to read current sensing data may be used as a digital receive input, and an output that may be used for switching power to a heater element may be used as a digital output. Additionally or alternatively, in some such example embodiments, a heater connection point(s) and/or other interface that may be used to provide power to and/or otherwise control a cartridge may be used to sample an equivalent resistance and/or other characteristic of the cartridge 328, which may be representative of control information that may be carried by the cartridge 328 in accordance with some example embodiments, such as those illustrated in and described further herein below with respect to FIGS. 7 and 8.

The cartridge 328 may carry control information that may be read by the processing circuitry 310 (e.g., via cartridge interface 318). For example, in some embodiments, such as those illustrated in and described herein below with respect to FIGS. 5 and 6, the cartridge 328 may comprise a memory, which may store control information that may be read by the processing circuitry 310. Additionally or alternatively, in some example embodiments, such as those illustrated in and described further herein below with respect to FIGS. 7 and 8, the cartridge 328 may carry control information in the form of a measurable characteristic, such as an equivalent resistance, that may be measured and/or otherwise read by the processing circuitry 310. In this regard, a measurable characteristic of the cartridge 328 may be representative of the control information such that cartridges 328 having various equivalent resistance values and/or other measurable characteristic values may be used to provide different control information to the control body of an aerosol delivery device.

In some example embodiments, the cartridge 328 may comprise a cartridge including a consumable arrangement, which may include an aerosol precursor composition and at least one heating element, such as heating element 134, operably engaged therewith. In this regard, the cartridge 328 of such example embodiments may comprise an embodiment of a cartridge, such as cartridge 104 or cartridge 204, that may be engaged with a control body to enable the generation of an inhalable substance through heating of aerosol precursor composition that may be included in the cartridge 328.

Alternatively, in some example embodiments, the cartridge 328 may comprise an accessory cartridge that does not comprise aerosol precursor composition or a heating element. In this regard, in embodiments in which the cartridge 328 is embodied as an accessory cartridge, the cartridge 328 may be a dedicated control cartridge that may be configured to provide control information to a control body to cause the control body to perform an action based at least in part on the control information in accordance with one or more example embodiments.

The processing circuitry 310 may be configured to read control information that may be carried by the cartridge 328 via the cartridge interface 318. The processing circuitry 310 may be further configured to perform an action based at least in part on the control information.

For example, in some embodiments, the cartridge 328 may carry control information comprising indicia of a configuration setting update, and the processing circuitry may be configured to modify a configuration of the aerosol delivery device in accordance with the configuration setting update. The configuration setting update may include an update to any adjustable operating parameter that may relate to operation of an aerosol delivery device.

For example, the configuration setting update may comprise an update to a configuration setting for an element of the user interface 316, such as the functionality of an LED and/or other indicator(s) that may be provided by the user interface 316, a vibrator and/or other haptic feedback device, and/or other user interface element. In embodiments in which the user interface 316 includes a vibrator and/or other haptic feedback device, it will be appreciated that any of a variety of haptic feedback configuration settings may be modified. For example, a vibration strength of a haptic feedback device may be increased or decreased, haptic feedback (e.g., for various event notifications) can be activated/deactivated, and/or the like.

As a further example, the configuration setting update may comprise an updated heating profile configuration. As another example, the configuration setting update may comprise an update to an aerosol precursor composition vaporization setting, such as a configuration defining an amount of aerosol precursor composition that is vaporized per puff, and/or other configuration setting that may relate to the vaporization of aerosol precursor composition. As still a further example, the configuration setting update may comprise a puff control setting, such as a number of puffs that are allowed within a period of time and/or for a single smoking session, a minimum interval of time that must elapse between puffs, and/or other setting that may govern device behavior with respect to user puffs. In some embodiments, the configuration setting update may comprise a battery management setting, such as a configuration relating to charging of a battery and/or a configuration that may regulate consumption of the battery.

In some example embodiments, control information that may be carried by the cartridge 328 may comprise a software update for an aerosol delivery device. For example, in some embodiments, such as some embodiments illustrated in and discussed further herein below with respect to FIGS. 5 and 6, a software update may be stored on a memory of the cartridge 328. The processing circuitry 310 may accordingly access the software update and install the software update on the aerosol delivery device, such as on the memory 314 and/or other memory that may be implemented on a control body and/or other portion of an aerosol delivery device.

The cartridge 328 of some example embodiments may carry control information configured to cause the processing circuitry 310 to execute a diagnostic program for testing functionality of the aerosol delivery device. In such embodiments, the processing circuitry 310 can execute the diagnostic program in response to reading the control information to perform an automated self-test of functionality of the aerosol delivery device. In some such embodiments, the diagnostic program may be stored on the cartridge 328, such as in a memory that may be included in some embodiments of the cartridge 328, such as those illustrated in and described below with respect to FIGS. 5 and 6. Alternatively, in some embodiments, the diagnostic program may be implemented on the control body (e.g., stored on memory 314) and the control information may be configured to cause the processing circuitry 310 to execute the diagnostic program.

In some example embodiments, the cartridge 328 may carry control information configured to trigger a reset of control data for the aerosol delivery device. In such embodiments, the processing circuitry 310 may be configured to reset the control data to a default state in response to reading the control information. For example, in some embodiments, the control data may comprise configuration settings that may control operation of the aerosol delivery device, such as by way of non-limiting example, a configuration setting or an element of the user interface 316, a heating profile configuration, an aerosol precursor composition vaporization setting, a puff control setting, a battery management setting, and/or the like.

FIG. 4 illustrates a flowchart according to an example method for providing control information to an aerosol delivery device via a cartridge, such as cartridge 328, in accordance with some example embodiments of the present disclosure. In this regard, FIG. 4 illustrates operations that may be performed by a control body of an aerosol delivery device in accordance with some example embodiments. One or more of processing circuitry 310, processor 312, memory 314, user interface 316, or cartridge interface 318 may, for example, provide means for performing one or more of the operations illustrated in and described with respect to FIG. 4.

Operation 400 may comprise the control body reading control information carried by the cartridge 328. For example, in embodiments, such as those illustrated in and described below with respect to FIGS. 5 and 6, operation 400 may comprise reading control information that may be stored on a memory of the cartridge 328 of some embodiments. As another example, in some embodiments, such as those illustrated in and described below with respect to FIGS. 7 and 8, operation 800 may comprise measuring a characteristic, such as an equivalent resistance value, of the cartridge 328, which may convey the control information.

Operation 410 may comprise the control body performing an action based at least in part on the control information. The type of action performed may vary depending on the control information read in operation 400. By way of non-limiting example, operation 410 may comprise modifying a configuration setting, installing a software update, executing a diagnostic program, resetting control data, and/or the like.

Referring now to FIG. 5, FIG. 5 illustrates an example aerosol delivery system 500 comprising a control body 502 and a cartridge 504 carrying control information stored on a memory 520 in accordance with some example embodiments of the present disclosure. The control body 502 and cartridge 504 may be removably engaged to support reading of control information carried by the cartridge 504.

The control body 502 may, for example, comprise an embodiment of the control body 102 and/or control body 202. The control body 502 of some example embodiments may include an embodiment of apparatus 300. Thus, for example, the control body 502 may include processing circuitry 510, which may comprise an embodiment of processing circuitry 310, and a cartridge interface 514, which may comprise an embodiment of cartridge interface 318. The control body 502 may further comprise memory 512. In some example embodiments, memory 512 may comprise an embodiment of memory 314 and, as such, may be at least partially embodied on processing circuitry 510. Additionally or alternatively, in some example embodiments, the memory 512 may comprise a memory that may be embodied separately from the processing circuitry 510. Regardless of implementation, the memory 512 may comprise any memory device, which can be configured to store control data, such as a program (e.g., control software) that may be executed by processing circuitry 510, a configuration setting that may govern an operating parameter of an aerosol delivery device, and/or the like.

The cartridge 504 may comprise an embodiment of the cartridge 328. The cartridge 504 may include memory 520, which may be configured to store control information that may be read by processing circuitry 510. By way of non-limiting example, the memory 520 may comprise flash memory. However, it will be appreciated that other forms of memory may be used in addition to or in lieu of flash memory within the scope of the disclosure.

In some embodiments, the cartridge 504 may further comprise controller 522. The controller 522 may, for example, comprise a microprocessor, microcontroller, ASIC, FPGA, some combination thereof, or the like. In embodiments including controller 522, the controller 522 may be configured through hardware or a combination of hardware or software to facilitate reading of control information that may be stored on the memory 520 by the processing circuitry 510. For example, in some embodiments, the controller 522 may be configured to facilitate active communication by the cartridge 504 with the processing circuitry 510 and/or other element of control body 502. In this regard, the controller 522 of such example embodiments may be configured to send control information and/or other data to the control body 502 (e.g., via the control body interface 524) to enable the processing circuitry 510 to read the control information.

However, in some embodiments, the controller 522 may be omitted. In some embodiments in which the controller 522 is omitted, the processing circuitry 510 may be configured to access memory 520 (e.g., via a link between the cartridge interface 514 and control body interface 524) to read control information that may be stored on the memory 520.

The cartridge 504 may additionally include a control body interface 524. The control body interface 525 may comprise any interface which may be compatible with cartridge interface 514 to enable the processing circuitry 510 to access control information stored on memory 520 and/or to enable the communication of the control information from the cartridge 504 to the control body 502.

For example, in some embodiments, the control body interface 524 may comprise a communication or data interface enabling data communication between the control body 502 and cartridge 504. In some such example embodiments, the control body interface 524 may, for example, comprise a wireline communication interface, such as a serial communication interface, USB interface, FireWire interface, and/or other wireline communication interface that may be used to communicate data between two entities. Additionally or alternatively, in some embodiments in which the control body interface 524 may comprise a communication or data interface, the control body interface 524 may provide a wireless communication interface, which may be configured to use a wireless communications technology, such as Wi-Fi and/or other IEEE 802.11 technology, Bluetooth, Zigbee, wireless USB, NFC, RF-ID, and/or other wireless communications technology that may be used to convey data from one entity (e.g., the cartridge 504) to another (e.g., to the control body 502).

Additionally or alternatively, in some example embodiments, the control body interface 524 may comprise an interface that may be used to receive power and/or control instructions from the control body 502. For example, the control body interface 524 of some such example embodiments may comprise one or more heater connection points that may be repurposed to provide a serial interface, which may be used to convey data between the control body 502 and cartridge 504.

In some example embodiments, the cartridge 504 may further comprise a consumable arrangement, which may include an aerosol precursor composition and at least one heating element, such as heating element 134, operably engaged therewith. In this regard, the cartridge 504 of such example embodiments may comprise an embodiment of a cartridge, such as cartridge 104 or cartridge 204, that may be engaged with a control body to enable the generation of an inhalable substance through heating of aerosol precursor composition that may be included in the cartridge 504. Alternatively, in some example embodiments, the cartridge 504 may comprise an accessory cartridge that does not comprise aerosol precursor composition or a heating element. In this regard, in embodiments in which the cartridge 504 is embodied as an accessory cartridge, the cartridge 504 may be a dedicated control cartridge that may be configured to provide control information to the control body 502 to cause the control body 502 to perform an action based at least in part on the control information in accordance with one or more example embodiments.

In some example embodiments, a battery that may be embodied on the control body 502 may provide power to one or more elements of the cartridge 504, such as via a connection that may be established between cartridge interface 514 and control body interface 524 when the control body 502 and cartridge 504 are engaged. For example, in some embodiments in which the memory 520 may draw power to support read and/or write access, power that may be provided by the control body 502 may be used to power the memory 520. As a further example, in embodiments in which the cartridge 504 includes a controller 522, the power may be used to power the controller 522. As still a further example, in embodiments in which the cartridge 504 comprises a consumable arrangement, the control body 502 may provide power that may be used to enable operation of a heating element.

FIG. 6 illustrates a flowchart according to an example method for providing control information to an aerosol delivery device via a cartridge carrying control information stored on a memory in accordance with some example embodiments of the present disclosure. In this regard, FIG. 6 illustrates operations that may be performed by control body 502 within the aerosol delivery system 500 in accordance with some example embodiments. One or more of processing circuitry 310, processor 312, memory 314, cartridge interface 318, processing circuitry 510, memory 512, cartridge interface 514, memory 520, controller 522, or control body interface 524 may, for example, provide means for performing the operations illustrated in and described with respect to FIG. 6.

Operation 600 may comprise the control body 502 reading control information stored on the memory 520. For example, in some embodiments, operation 600 may comprise the processing circuitry 510 accessing the memory 520 (e.g., via cartridge interface 514 and control body interface 524) and reading the control information from the memory 520. Additionally or alternatively, in some example embodiments, control information that may be stored on the memory 520 may be provided to the control body 502 (e.g., by controller 522), and the processing circuitry 510 may receive and read the provided control information. Operation 600 can accordingly correspond to an embodiment of operation 400 in which control information is stored on a memory embodied on a cartridge.

Operation 610 may comprise the control body 502 (e.g., the processing circuitry 510) performing an action based at least in part on the control information. The type of action performed may vary depending on the control information read in operation 600. By way of non-limiting example, operation 610 may comprise modifying a configuration setting, installing a software update, executing a diagnostic program, resetting control data, and/or the like. For example, in embodiments in which a software update is stored on memory 520, operation 610 may comprise installing the software update on memory 512. Operation 610 may accordingly correspond to an embodiment of operation 410.

FIG. 7 illustrates an example aerosol delivery system 700 comprising a control body 702 and a cartridge 704 carrying control information in the form of an equivalent resistance value 710 in accordance with some example embodiments of the present disclosure. The control body 702 and cartridge 704 may be removably engaged to support reading of control information carried by the cartridge 704. The control body 702 may, for example, comprise an embodiment of the control body 102 and/or control body 202, and, in some example embodiments, may include an embodiment of the apparatus 300. The cartridge 704 may comprise an embodiment of the cartridge 328.

In some example embodiments, the cartridge 704 may comprise a heater 712, which may provide part of a consumable arrangement, which may further include aerosol precursor composition. In this regard, the cartridge 704 of some example embodiments may comprise an embodiment of a cartridge, such as cartridge 104 or cartridge 204, that may be engaged with a control body to enable the generation of an inhalable substance through heating of aerosol precursor composition that may be included in the cartridge 704 with the heater 712. Alternatively, in some example embodiments, the cartridge 704 may comprise an accessory cartridge in which the heater 712, aerosol precursor composition, and/or other elements of a consumable arrangement may be omitted. In embodiments in which the cartridge 704 is embodied as an accessory cartridge, the cartridge 704 may be a dedicated control cartridge that may be configured to provide control information to the control body 702 to cause the control body 702 to perform an action based at least in part on the control information in accordance with one or more example embodiments.

The control body 702 may comprise microcontroller 720, which may, for example, comprise an embodiment of processing circuitry 310. The microcontroller 720 may be configured to execute one or more software blocks that may control aspects of operation of an aerosol delivery device. The software blocks may comprise one or more software blocks that may be stored on a memory, such as memory 314, that may be included in the microcontroller 720 and/or may comprise one or more software blocks that may be stored on a memory that may be external to the microcontroller 720. By way of non-limiting example, the software blocks may include a software block related to operation of user interface elements (e.g., aspects of the user interface 316), a software block for controlling a heater, such as heater 712, that may be implemented on a cartridge that maybe engaged with control body 702, a software block for depletion/counting functionality as may relate to consumption of aerosol precursor composition form a cartridge, a software block for regulating charging of the battery, and/or the like.

The microcontroller 720 of some example embodiments may include one or more interfaces, which may, for example, comprise one or more aspects of the cartridge interface 318 and/or one or more aspects of the user interface 316. For example, the interfaces may include an interface 722 that may be used to provide power to a cartridge, such as cartridge 704. In the example of FIG. 7, a pulse-width modulation (PWM) interface that may be configured to utilize various PWM techniques for switching and/or otherwise regulating current and/or power that may be provided to a cartridge or element thereof, such as heater 712 is illustrated.

The microcontroller 720 may further include an interface 724 that may be configured to read current sensing data that may be associated with operation of a heating element (e.g., heater 712) and/or other component that may be implemented on a cartridge comprising a consumable arrangement. The interface 724 may comprise an analog-to-digital converter (ADC), which may be used to convert analog current values into digital values. However, it will be appreciated that other arrangements that may be used to read current sensing data may be used in addition to or in lieu of an ADC in accordance with various embodiments.

The interfaces 722 and 724 may provide heater connection points, which may used to provide power to and/or otherwise control operation of a cartridge and/or component thereof (e.g., operation of heater 712) providing a consumable arrangement. For example, the interfaces 722 and 724 may be configured to operatively engage with heater terminals, such as heater terminals 138 that may be implemented on a cartridge comprising a consumable arrangement. In accordance with some example embodiments, the interfaces 722 and 724 may be used to measure an equivalent resistance value of the cartridge 704. For example, in some embodiments, the microcontroller 720 may be configured to sample the heater connection points (e.g., via interfaces 722 and 724) (e.g., continuously) at a defined rate during operation of the aerosol delivery device. As another example, in some embodiments, the microcontroller 720 may sample the heater connection points in response to a sensor input, such as a sensor configured to detect the presence of cartridge 704. Sampling of the heater connection points can accordingly be used to measure the equivalent resistance value of the cartridge 704.

The microcontroller 720 can determine an action (if one exists) that has a defined correlation to the measured equivalent resistance value of the cartridge 704. In this regard, some example embodiments can provide a plurality of preconfigured actions, each of which may have a defined correlation with a specific equivalent resistance value and/or other measurable characteristic of a cartridge. The microcontroller 720 can accordingly be configured to look up a measured equivalent resistance value of the cartridge 704, such as in a data structure containing equivalent resistance values and their associated actions that may be maintained on memory 314 and/or other memory that may be accessible to the microcontroller 720, to determine the action correlated to the measured equivalent resistance value. The microcontroller 720 can then perform the determined action.

In this regard, an equivalent resistance value and/or other measurable characteristic of the cartridge 704 may be representative of the control information such that cartridges having various equivalent resistance values and/or other measurable characteristic values may be used to provide different control information to the control body 702. For example, different equivalent resistance values may be associated with different configuration setting updates. As a further example, an equivalent resistance value may have a defined association with execution of a diagnostic program (e.g., an automated self-test function). As another example, an equivalent resistance value may have a defined association with a reset function that may be used to reset control data of the control body 702 to a default state.

FIG. 8 illustrates a flowchart according to an example method for providing control information to an aerosol delivery device via a cartridge carrying control information in the form of an equivalent resistance value in accordance with some example embodiments of the present disclosure. In this regard, FIG. 8 illustrates operations that may be performed by control body 702 within the aerosol delivery system 700 in accordance with some example embodiments. One or more of processing circuitry 310, processor 312, memory 314, cartridge interface 318, microcontroller 720, or interfaces 722 and 724 may, for example, provide means for performing the operations illustrated in and described with respect to FIG. 8.

Operation 800 may comprise the control body 702 measuring the equivalent resistance value 710 of the cartridge 704. For example, in some embodiments, operation 800 may comprise the microcontroller 720 sampling heater connection points via interfaces 722 and 724 to determine the equivalent resistance value 710. Operation 800 can accordingly correspond to an embodiment of operation 400 in which control information may be carried in the form of an equivalent resistance value.

Operation 810 may comprise the control body 702 (e.g., the microcontroller 720) determining an action having a defined correlation to the equivalent resistance value. Operation 820 may comprise the control body 702 (e.g., the microcontroller 720) performing the action determined in operation 810. Operation 820 may accordingly correspond to an embodiment of operation 410. The type of action performed may vary depending on the equivalent resistance value 710, as different actions may be associated with different resistance values.

In some example embodiments, a control body (e.g., processing circuitry 310 and/or microcontroller 720 implemented on the control body) may be configured to discern a standard consumable cartridge (e.g., a cartridge comprising a consumable arrangement that does not carry control data) from a control cartridge, which may or may not include a consumable arrangement depending on embodiment, carrying control information based at least in part on an equivalent resistance value and/or other measurable characteristic of the cartridge. For example, a standard consumable cartridge may have an associated equivalent resistance value, such as may be associated with a resistance of the heater 712. The control body of some example embodiments may be configured to measure an equivalent resistance value of a cartridge engaged with the control body and compare the measured equivalent resistance value to a reference resistance value associated with a standard cartridge comprising a consumable arrangement. If the measured equivalent resistance value is substantially equal to the reference resistance value, then the cartridge may be determined to be a standard cartridge that does not carry control information. If, however, the measured equivalent resistance value is not substantially equal to the reference resistance value, the cartridge may be determined to carry control info Illation, and the control body may perform operations 810-820, as described above to perform alternate programming of the aerosol delivery device.

While the embodiments of FIGS. 7 and 8 have been described with respect to the usage of equivalent resistance values for carrying control information, it will be appreciated that techniques for measuring equivalent resistance values and using equivalent resistance values illustrated in and discussed with respect to FIGS. 7 and 8 may be applied mutatis mutandis to other measurable characteristic of a cartridge that may be selectively varied for the purpose of conveying control information and programming an aerosol delivery device within the scope of the disclosure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery system, comprising:
a control body comprising processing circuitry; and
an accessory cartridge carrying control information that is readable by the processing circuitry;
wherein the control body further comprises a cartridge engaging portion with which the control body is alternately, removably engageable with an aerosol cartridge with a heating element and an aerosol precursor composition, and the accessory cartridge without a heating element or aerosol precursor composition, wherein the control body and the aerosol cartridge when engaged form an aerosol delivery device; and
wherein the processing circuitry is configured to at least:
read the control information carried by the accessory cartridge when the control body and the accessory cartridge are engaged; and
perform an action based on the control information.

2. The aerosol delivery system of claim 1, wherein:
the control information comprises indicia of a configuration setting update; and
the processing circuitry being configured to perform the action includes being configured to modify a configuration of the aerosol delivery device in accordance with the configuration setting update.

3. The aerosol delivery system of claim 2, wherein the aerosol delivery device includes a light emitting diode (LED) indicator, and the configuration setting update comprises one or more of a configuration setting for the LED indicator, a heating profile configuration for the heating element, an aerosol precursor composition vaporization setting for the aerosol precursor composition, or a puff control setting.

4. The aerosol delivery system of claim 1, wherein:
the control information comprises a software update for the aerosol delivery device;
the accessory cartridge comprises a first memory storing the software update;
the control body comprises a second memory; and
the processing circuitry being configured to perform the action includes being configured to install the software update on the second memory.

5. The aerosol delivery system of claim 1, wherein:
the control information is configured to cause the processing circuitry to execute a diagnostic program for testing functionality of the aerosol delivery device; and
the processing circuitry being configured to perform the action includes being configured to execute the diagnostic program in response to the control information.

6. The aerosol delivery system of claim 1, wherein:
the control information is configured to trigger a reset of control data for the aerosol delivery device, the control data being separate from the control information; and
the processing circuitry being configured to perform the action includes being configured to reset the control data to a default state in response to the control information.

7. The aerosol delivery system of claim 1, wherein the accessory cartridge comprises a memory storing the control information.

8. The aerosol delivery system of claim 1, wherein:
the control information comprises an equivalent resistance value of the accessory cartridge, wherein the equivalent resistance value is measurable by the processing circuitry when the control body and the accessory cartridge are engaged;
the processing circuitry being configured to read the control information includes being configured to measure the equivalent resistance value;
the processing circuitry is further configured to determine an action having a defined correlation to the equivalent resistance value; and
the processing circuitry being configured to perform the action includes being configured to perform the action having the defined correlation to the equivalent resistance value.

9. The aerosol delivery system of claim 8, wherein:
the processing circuitry is further configured to compare the equivalent resistance value to a reference resistance value associated with the aerosol cartridge; and
the processing circuitry is configured to determine and perform the action having the defined correlation to the equivalent resistance value only in an instance in which the equivalent resistance value is not substantially equal to the reference resistance value.

10. A control body comprising:
a cartridge engaging portion with which the control body is alternately, removably engageable with an aerosol cartridge with a heating element and an aerosol precursor composition, and an accessory cartridge without a heating element or aerosol precursor composition, wherein the control body and the aerosol cartridge when engaged form an aerosol delivery device; and
processing circuitry configured to at least:
read control information carried by the accessory cartridge when the accessory cartridge is engaged with the control body; and
perform an action based on the control information.

11. The control body of claim 10, wherein the processing circuitry is further configured to read control information at least in part by reading control information stored on a memory of the accessory cartridge.

12. The control body of claim 10, wherein the processing circuitry is further configured to:
read the control information at least in part by measuring an equivalent resistance value of the accessory cartridge;
determine an action having a defined correlation to the equivalent resistance value; and
perform the action by performing the action having the defined correlation to the equivalent resistance value.

13. An accessory cartridge configured for use with a control body of an aerosol delivery device, the accessory cartridge comprising:
a control body engaging portion with which the accessory cartridge is removably engageable with the control body of the aerosol delivery device, control body being alternately, removably engageable with an aerosol cartridge with a heating element and an aerosol precursor composition, and the accessory cartridge without a heating element or aerosol precursor composition, wherein the control body and the aerosol cartridge when engaged form the aerosol delivery device;
wherein the accessory cartridge is configured to carry control information readable by the control body when the control body and the accessory cartridge are engaged, the control body being configured to perform an action based on the control information.

14. The accessory cartridge of claim 13, further comprising a memory storing the control information.

15. The accessory cartridge of claim 13, wherein the accessory cartridge has an equivalent resistance value measurable when the control body and the accessory cartridge are engaged, and wherein the control information comprises the equivalent resistance value.

16. A method for providing control information to a control body of an aerosol delivery device, the method comprising the steps of:
engaging an accessory cartridge with the control body comprising a cartridge engaging portion with which the control body is alternately, removably engageable with an aerosol cartridge with a heating element and an aerosol precursor composition, and the accessory cartridge without a heating element or aerosol precursor composition, wherein the control body and the aerosol cartridge when engaged form an aerosol delivery device;
reading, by processing circuitry of the control body, control information carried by the accessory cartridge; and
performing, by the processing circuitry, an action based at least in part on the control information.

17. The method of claim 16, wherein:
the control information comprises indicia of a configuration setting update; and
performing the action comprises modifying a configuration of the aerosol delivery device in accordance with the configuration setting update.

18. The method of claim 17, wherein the aerosol delivery device includes a light emitting diode (LED) indicator, and the configuration setting update comprises one or more of a configuration setting for the LED indicator, a heating profile configuration for the heater heating element, an aerosol precursor composition vaporization setting for the aerosol precursor composition, or a puff control setting.

19. The method of claim 16, wherein the control information comprises a software update for the aerosol delivery device, and wherein performing the action comprises installing the software update on a memory of the control body.

20. The method of claim 16, wherein the control information is configured to cause the control body to execute a diagnostic program for testing functionality of the aerosol delivery device, and wherein performing the action comprises executing the diagnostic program in response to reading the control information.

21. The method of claim 16, wherein the control information is configured to trigger a reset of control data for the aerosol delivery device, the control data being separate from the control information, and wherein performing the action comprises resetting the control data to a default state in response to reading the control information.

22. The method of claim 16, wherein reading the control information comprises accessing control information stored on a memory of the accessory cartridge.

23. The method of claim 16, wherein:
the control information comprises an equivalent resistance value of the accessory cartridge;
reading the control information comprises measuring the equivalent resistance value; and
the method further comprises the control body:
determining an action having a defined correlation to the equivalent resistance value; and performing the action having the defined correlation to the equivalent resistance value.

24. The method of claim 23, wherein the method further comprises the control body:
comparing the equivalent resistance value to a reference resistance value associated with the aerosol cartridge; and
determining the action having the defined correlation to the equivalent resistance value and performing the action only in an instance in which the equivalent resistance value is not substantially equal to the reference resistance value.

25. The aerosol delivery system of claim 2, wherein the aerosol delivery device includes a haptic feedback device, and the configuration setting update comprises one or more of a haptic feedback configuration setting for the haptic feedback device, a heating profile configuration for the heating element, an aerosol precursor composition vaporization setting for the aerosol precursor composition, or a puff control setting.

26. The aerosol delivery system of claim 2, wherein the aerosol delivery device includes a battery, and the configuration setting update comprises one or more of a heating profile configuration for the heating element, an aerosol precursor composition vaporization setting for the aerosol precursor composition, a puff control setting, or a battery management setting for the battery.

27. The method of claim 17, wherein the aerosol delivery device includes a haptic feedback device, and the configuration setting update comprises one or more of a haptic feedback configuration setting for the haptic feedback device, a heating profile configuration for the heating element, an aerosol precursor composition vaporization setting for the aerosol precursor composition, or a puff control setting.

28. The method of claim 17, wherein the aerosol delivery device includes a battery, and the configuration setting update comprises one or more of a heating profile configuration for the heating element, an aerosol precursor composition vaporization setting for the aerosol precursor composition, a puff control setting, or a battery management setting for the battery.

* * * * *